(12) United States Patent
Radmer et al.

(10) Patent No.: US 7,780,636 B2
(45) Date of Patent: Aug. 24, 2010

(54) PORTABLE DRUG DELIVERY DEVICE HAVING AN ENCAPSULATED NEEDLE

(75) Inventors: Jim Radmer, Fredensborg (DK); Henrik Sonderskov Klint, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 1019 days.

(21) Appl. No.: 11/326,550

(22) Filed: Jan. 5, 2006

(65) Prior Publication Data
US 2006/0200073 A1    Sep. 7, 2006

Related U.S. Application Data

(63) Continuation of application No. PCT/DK2004/000463, filed on Jun. 29, 2004.

(60) Provisional application No. 60/487,859, filed on Jul. 16, 2003, provisional application No. 60/487,090, filed on Jul. 14, 2003.

(30) Foreign Application Priority Data

Jul. 8, 2003    (DK) ............................... 2003 01041
Jul. 8, 2003    (EP) ................................. 03388049

(51) Int. Cl.
*A61M 5/178* (2006.01)

(52) U.S. Cl. .................... 604/192; 604/198; 604/171; 604/200; 604/201; 604/205

(58) Field of Classification Search ............ 604/980.1, 604/93.01, 198, 192, 196, 180, 890.1, 171, 604/205

See application file for complete search history.

(56) References Cited

U.S. PATENT DOCUMENTS

| 2,605,765 | A |   | 8/1952 | Kollsman |
| 3,587,575 | A | * | 6/1971 | Lichtenstein ................ 604/195 |
| 3,645,253 | A | * | 2/1972 | Goverde et al. ............. 600/578 |
| 4,340,048 | A |   | 7/1982 | Eckenhoff |

(Continued)

FOREIGN PATENT DOCUMENTS

DE           2552446           11/1975

(Continued)

OTHER PUBLICATIONS

Notification Concerning Transmittal of Copy of International Preliminary Report on Patentability (Chapter 1 of Patent Cooperation Treaty) Mailed Jan. 19, 2006.

*Primary Examiner*—Nicholas D Lucchesi
*Assistant Examiner*—Laura A Bouchelle
(74) *Attorney, Agent, or Firm*—Marc A. Began (57) ABSTRACT

The present invention relates to medical devices which are adapted for application to a skin surface of a user and comprise a transcutaneous device which is supplied in a sterile condition. Thus, a medical device is provided, comprising a mounting surface adapted for application to the skin of a subject, a first portion having a first end adapted to penetrate the skin of the subject, and a second portion in fluid communication with the first portion and having a second end. The device further comprises enclosure means being transformable from an initial configuration encapsulating the first and second portions in an initial aseptic state, to a second configuration in which the ends of the first and second portions are allowed to communicate with the exterior through the enclosure means, wherein the enclosure means does not enclose the mounting surface.

5 Claims, 8 Drawing Sheets

U.S. PATENT DOCUMENTS

| | | | |
|---|---|---|---|
| 4,552,561 A | 11/1985 | Eckenhoff et al. | |
| 5,169,390 A | 12/1992 | Athayde et al. | |
| 5,527,288 A | 6/1996 | Gross et al. | |
| 5,616,132 A * | 4/1997 | Newman | 604/185 |
| 5,814,020 A | 9/1998 | Gross | |
| 5,851,197 A | 12/1998 | Marano et al. | |
| 5,858,001 A * | 1/1999 | Tsals et al. | 604/135 |
| 5,931,814 A | 8/1999 | Alex et al. | |
| 5,957,895 A | 9/1999 | Sage et al. | |
| 6,045,534 A | 4/2000 | Jacobsen et al. | |
| 6,074,369 A | 6/2000 | Sage et al. | |
| 6,126,637 A | 10/2000 | Kriesel et al. | |
| 6,280,148 B1 | 8/2001 | Zengerle et al. | |
| 6,302,869 B1 | 10/2001 | Klitgaard | |
| 6,740,059 B2 | 5/2004 | Flaherty | |
| 2002/0010423 A1 | 1/2002 | Gross et al. | |
| 2002/0095138 A1 * | 7/2002 | Lynch et al. | 604/890.1 |
| 2002/0123719 A1 | 9/2002 | Lavi et al. | |

FOREIGN PATENT DOCUMENTS

| | | |
|---|---|---|
| EP | 1177802 | 7/2001 |
| WO | 02/15965 | 8/2001 |
| WO | 02/40083 | 11/2001 |
| WO | 03/090509 | 4/2003 |

* cited by examiner

PORTABLE DRUG DELIVERY DEVICE HAVING AN ENCAPSULATED NEEDLE

The present invention generally relates to devices which are adapted for application to a skin surface of a user and comprise a transcutaneous device such as a needle or a needle-like member which is supplied in a sterile condition, as well as transcutaneous devices suitable for being used therewith. In specific aspects, the invention relates to such devices comprising transcutaneous devices adapted for insertion at a selected site within the body of a subject for subcutaneous, intravenous, intramuscular or intradermal delivery of a drug to the subject, the needles also being adapted for connection to a reservoir for containing a drug.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniences, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain. Although not relating specifically to infusion pumps, U.S. Pat. No. 5,851,197 discloses an injector in which an infusion set comprising a skin-mountable surface with a protruding needle can be mounted, the injector upon actuation driving the entire infusion set into contact with a skin portion whereby the needle is inserted through the skin.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Although the automatic needle insertion means adds convenience for the user and may serve to overcome needle fear, such means also adds to the complexity and thus to the cost of the device, they may reduce the reliability, just as they may add to the bulkiness of the device.

In order to avoid e.g. drug leaking into the needle prior to use, some delivery devices are provided with needles which are brought into fluid communication with the reservoir just prior to use, e.g. as disclosed in U.S. Pat. Nos. 5,858,001 and 5,957,895 in which the infusion needle is connected to the drug reservoir during actuation of the needle insertion means.

Instead of using a traditional steel needle, WO 02/40083 and WO 03/090509 disclose a fluid delivery device in which the traditional needle has been replaced by a soft cannula in combination with an insertion needle. U.S. Pat. No. 6,740,059 discloses a fluid delivery device in which the traditional needle has been replaced by a micro needle array.

For all of the above types of devices the needle or other transcutaneous device to be introduced into the user as well as the drug to be infused will have to meet specific requirements as to sterility, such requirements adding to the costs and complexity of manufacture.

DISCLOSURE OF THE INVENTION

Having regard to the above-identified problems, it is an object of the present invention to provide a transcutaneous device arrangement which allows a medical delivery means to be manufactured in a convenient and cost-effective manner. The transcutaneous device arrangement should contribute in providing a medical delivery device which allows for easy and swift needle operation yet being reliable in use. It is a further object of the present invention to provide a transcutaneous device unit which allows a medical device (or a component therefore) comprising a transcutaneous device to be manufactured in a convenient and cost-effective manner. The transcutaneous device unit should contribute in providing a drug delivery device which allows for easy and swift needle operation yet being reliable in use.

Thus, corresponding to a first aspect, a medical device is provided, comprising a mounting surface adapted for application to the skin of a subject, a transcutaneous device portion having a first end adapted to penetrate the skin of the subject and forming a first conduit portion, and an inlet portion in fluid communication with the first portion, having a second end and forming a second conduit portion. The device further comprises enclosure means being transformable from an initial configuration encapsulating the first and second conduit portions in an initial sterile (or aseptic) state, to a second configuration in which the ends of the first and second conduit portions are allowed to communicate with the exterior through the enclosure means, wherein the enclosure means does not enclose the mounting surface. In exemplary embodiments the enclosure means is arranged in the vicinity of the first and second ends. In the remaining disclosure of the present invention and in the claims the shorter form "first portion" and "second portion" is used for "first conduit portion" respectively "second conduit portion".

The term "transformable" covers all situations in which a portion of the enclosure means is broken, penetrated or removed to allow communication between an end portion and the exterior, e.g. a portion may be moved relative to the enclosure means, the enclosure means may be moved relative to the first or second portion or an external component may be moved into communication with the one of the portions through the enclosure means. The type of transformation may be different for the two portions. By the term "exterior" is meant any space or structure which initially was exterior to the enclosure means and the sterile portions. The term "vicinity" indicates that the enclosure means are arranged relative close to the enclosed needle portions, e.g. within a distance of less than 10 mm or less than 5 mm.

The transcutaneous device (which with the same meaning may also be termed a transcutaneous access device or a transcutaneous access tool) may be in the form of a pointed hollow infusion needle (which may also form the second portion), a micro needle array, or a combination of a relatively flexible per se blunt cannula or sensor device with a pointed insertion needle may provide a pointed transcutaneous device adapted to be inserted through the skin, the insertion needle being retractable after insertion of the blunt portion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle. It should be noted that a micro needle array may be defined as an intradermal device, however, in the present context the term transcutaneous device is used for a device which is adapted for penetrating at least a portion of the skin of a subject for the purpose of introducing a substance into the subject.

By this arrangement a separate unit is provided comprising a sterile, double-ended structure which can be mounted in combination with one or more further components to form a delivery device. In this way it is no longer necessary to sterilize the entire device just as it no longer necessary to keep the entire device sterile during storage. Indeed, in case the delivery device comprises a prefilled drug reservoir, the contents of this will have to provided in a sterile condition, however, in most cases it will suffice if the connecting portion of such a reservoir (e.g. a needle-penetratable septum) meets the requirements as to being "clean".

In an exemplary embodiment, the medical device is transformable between an initial state in which the first and second portions are encapsulated within the enclosure means in an initial sterile state, and a second state in which the inlet portion is allowed to communicate with the interior of a reservoir through a first portion of the enclosure means and the transcutaneous device portion projects from the mounting surface through a second portion of the enclosure means.

Corresponding to an embodiment of the invention a medical device is provided, comprising a housing including the mounting surface, a reservoir adapted to contain a liquid drug and comprising an outlet means allowing the second portion to be arranged in fluid communication with an interior of the reservoir, and expelling means for, in a situation of use, expelling a drug out of the reservoir and through the skin of the subject via the first end. Further, the medical device is transformable between an initial state in which the first and second portions are encapsulated by the enclosure means in an initial sterile state, and a second state in which the second portion is in fluid communication with the interior of the reservoir through a first portion of the enclosure means and the transcutaneous device portion projects from the mounting surface through a second portion of the enclosure means.

In a further embodiment of the invention a medical device is provided, comprising a pump unit having a reservoir adapted to contain a liquid drug and comprising an outlet means allowing the inlet portion to be arranged in fluid communication with an interior of the reservoir, and expelling means for, in a situation of use, expelling a drug out of the reservoir and through the skin of the subject via the transcutaneous device portion. Further, a receiving portion of the medical device and the reservoir unit also comprise mating coupling means allowing the pump unit to be secured to the medical device, the mating coupling means preferably being releasable.

Advantageously, fluid communication between the second inlet portion and the reservoir may be established when the pump unit is attached to the medical device. In addition, the transcutaneous device portion may be moved to a position in which it projects relative to the mounting surface when the pump unit is attached to the medical device. Alternatively, one or both of these operations are performed manually.

Depending on the actual configuration of the medical device, in an exemplary embodiment the first and second ends may be formed by a straight hollow needle or the ends of the needle may be arranged non-coaxially. For example, the above-described medical devices may comprise a generally U-formed hollow needle where the legs form the first and second needle portions. The U-formed needle may be moved linearly or pivotally between an initial state and an actuated state in which the ends of the needle are inserted in a drug reservoir respectively through the skin of a user. Alternatively, a needle unit forming the first and second needle portions, may be pivoted between an initial and an actuated state, the second needle portion being arranged corresponding to a pivoting axis for the needle unit, this allowing for axial connection to a drug reservoir.

For the above-described medical devices, the mounting surface may comprises adhesive means allowing for easy attachment to a skin surface of the user. Further, the mounting surface may be provided with an aperture through which at least a portion of the first needle portion may extend in a situation of use.

For all of the above-described medical devices, the enclosure means may be in the form of first and second collapsible cover means encapsulating the first respectively the second portions, the cover means being collapsible from an initial configuration surrounding the two portions to a collapsed configuration wherein the portions extend from the cover means. Advantageously, at least a portion of the cover means is penetratable to sterilizing gases yet provides a sterility barrier for the encapsulated needle portions. Further, the first and second collapsible cover means may be connected to allow for sterilization through a single opening.

In an embodiment of the invention a method of manufacturing a medical device is provided, comprising the steps of providing a transcutaneous device unit having a transcutaneous device portion with an end adapted to penetrate the skin of the subject, an inlet portion in fluid communication with the transcutaneous device portion and having a second end, and enclosure means encapsulating the first and second end portions in a sterile state, providing a base member comprising a mounting surface adapted for application to the skin of a subject, and assembling the transcutaneous device unit and the base member to provide a medical device.

In a further embodiment of the invention a method of manufacturing a medical device is provided, comprising the steps of providing a transcutaneous device unit having a transcutaneous device portion with a first end adapted to penetrate the skin of the subject, a second inlet portion in fluid communication with the first portion and having a second end, and enclosure means encapsulating the first and second end portions in a sterile state, providing a base member comprising a mounting surface adapted for application to the skin of a subject, providing a reservoir adapted to contain a liquid drug and having an outlet means allowing the inlet portion to be arranged in fluid communication with an interior of the reservoir, providing an expelling means for, in a situation of use, expelling a drug out of the reservoir and through the transcutaneous device portion, and assembling the needle unit, the base member, the reservoir and the expelling means to provide a medical device.

In the above methods of manufacturing, the individual components may be provided and assembled in any desirable and suitable order. After assembly, the assembled device may be enclosed in an outer packaging serving to protect the device and keep it in a "clean" state.

As appears, by these methods of manufacturing a medical device, only a small portion of the entire device will have to be sterilized. Further, the needle unit may be manufactured and/ or sterilized at a different location from the other component and shipped to the assembly site, this allowing for cost-effective manufacturing.

For all of the above embodiments in which a fluid communication is established between an inlet portion and a reservoir, this may be provided either via a direct connection between the inlet portion and the reservoir (e.g. by penetrating a septum of the reservoir) or indirectly (e.g. via connection to a structure in flow communication with the reservoir, e.g. the outlet of a suction pump drawing drug from a reservoir).

Corresponding to a second aspect of the invention, a transcutaneous device unit is provided, comprising a transcutaneous device portion having a first end and forming a first portion, an inlet portion in fluid communication with the first portion, having a second end and forming a second portion, as well as enclosure means arranged in the vicinity of the first and second ends and being transformable from an initial configuration encapsulating the first and second portions in an initial sterile (or aseptic) state, to a second configuration in which the ends of the first and second portions are allowed to communicate with the exterior, and wherein the first and second needle portions preferably are arranged non-coaxially.

By this arrangement a separate unit is provided comprising a sterile, double-ended structure (e.g. a double-ended needle) which can be mounted in combination with one or more further components to form a delivery device. In this way it is no longer necessary to sterilize the entire device just as it no longer necessary to keep the entire device sterile during storage. Indeed, in case the delivery device comprises a prefilled drug reservoir, the contents of this will have to be provided in a sterile condition, however, in most cases it will suffice if the connecting portion of such a reservoir (e.g. a needle-penetratable septum) meets the requirements as to being "clean".

In a first exemplary embodiment the enclosure means comprises a housing with at least one opening covered by cover means, the cover means allowing fluid communication to be established with the first and second portions, e.g. as discussed above.

To allow sterilization of the two portions after they has been enclosed, at least a portion of the cover means is advantageously penetratable to sterilizing gases yet provides a sterility barrier for the encapsulated portions.

The two portions may be individual elements connected to each other (e.g. a soft cannula and a therein mounted insertion needle) or by additional conduit means or they may be formed integrally, e.g. as a unitary hollow needle. Dependent upon the type of connection which is contemplated for the two portions, they may comprise an end allowing them to be introduced through the skin of a subject or a pierceable membrane, or they may be provided with connecting means allowing them to cooperate with corresponding connection means on e.g. a reservoir member.

In a second exemplary embodiment the enclosure means in the form of first and second collapsible cover means encapsulating the first respectively the second portion (i.e. the first and second collapsible cover means define first and second enclosures housing the first respectively the second portion), the cover means being collapsible from an initial configuration surrounding the first respectively the second needle portion to a collapsed configuration wherein the first respectively the second portion extends from the first respectively the second cover means. The collapsing means may be capable of returning to their initial configuration covering the respective portions (e.g. elastically deformable) or they may be may to a greater or lesser extent be permanently deformed to stay in a collapsed configuration (e.g. crushable) with the transcutaneous device portion or the inlet portion protruding permanently therefrom.

Advantageously, at least a portion of the first and second cover means is penetratable to sterilizing gases. Alternatively, a conduit may be provided allowing fluid communication between the first and second enclosures, the conduit comprising a portion penetratable to sterilizing gases. In this way only a single gas penetratable portion has to be provided just as the cover portions encapsulating the two portions can be optimized for that purpose.

In further exemplary embodiments the first and second collapsible cover means is provided by a common cover member, the common cover member advantageously also providing a conduit therebetween.

In other exemplary embodiments the two portions may be connected to a carrier which may be moveably connected to a further portion of the transcutaneous device unit, or the carrier may be adapted for being connected to an external structure, e.g. to a drug delivery device. To allow for a compact design the first and second needle portions may be arranged non-coaxially, e.g. in the form of a U-formed needle or a needle comprising one or more bend portions.

In a further embodiment of the invention a medical device is provided, comprising a needle unit as disclosed and discussed above, wherein the first portion comprises a transcutaneous device adapted to penetrate the skin of a subject. The device further comprises a housing having a mounting surface adapted for application to the skin of the subject, a reservoir adapted to contain a liquid drug and comprising an outlet means allowing the inlet portion to be arranged in fluid communication with an interior of the reservoir, and expelling means for, in a situation of use, expelling a drug out of the reservoir and through the skin of the subject via the transcutaneous device portion. In order to provide a fluid communication between the reservoir and the subject, the device is transformable between an initial state in which the first and second portions are encapsulated by the enclosure means in an initial sterile state, and a second state in which the second portion is in fluid communication with the interior of the reservoir through a first portion of the enclosure means and the transcutaneous device portion projects from the mounting surface through a second portion of the enclosure means.

To provide communication between the second needle portion and the reservoir, either or both of the reservoir and the second needle portions may be moveable relative to each other.

To provide the device with a "hidden transcutaneous device" the first portion may be moveable between an initial position in which the first portion is retracted within the housing, and a second position in which the first portion projects relative to the mounting surface. This movement may also be utilized to connect the inlet portion to the reservoir, for which purpose a generally U-formed hollow needle may be provided, the legs thereof forming the first and second needle portions. The U-formed needle may be moved either linearly or by a hinged arrangement just as either the entire needle unit or only the needle may be moved.

In a further embodiment a transcutaneous device unit is provided comprising a transcutaneous device portion having a first end adapted to penetrate the skin of a subject, the transcutaneous device portion forming a first portion, and an inlet portion in fluid communication with the first portion and having a second end, the inlet portion forming a second portion. The unit further comprises enclosure means being transformable from an initial configuration encapsulating the first and second portions in an initial sterile state, to a second configuration in which the first and second ends are allowed to communicate with the exterior through the enclosure means, wherein the transcutaneous device portion comprises an insertion needle and a cannula disposed on and being axially moveable relative to the insertion needle. Such a device unit may be used in any of the above-described applications.

The transcutaneous device portion advantageously has a first state in which the first end is in a retracted position within the enclosure means, and a second state in which the first end projects through a portion of the enclosure means, a distal end of the insertion needle projecting from a distal opening in the cannula. The unit may further have a third state in which the distal end of the insertion needle is retracted relative to the distal opening in the cannula.

In an embodiment the insertion needle comprises a proximal end forming the inlet portion, a seal being formed between the insertion needle and the cannula providing a fluid communication between the proximal end of the insertion needle and the distal opening in the cannula. In another embodiment a deflecting structure is provided, whereby a distal portion of the cannula is deflected relative to a proximal portion of the cannula as the cannula is moved from the retracted to the projecting position.

In a further embodiment of the invention a medical device is provided, comprising a transcutaneous device unit as disclosed and discussed above, wherein the first portion comprises a transcutaneous device adapted to penetrate the skin of a subject, and a mounting surface adapted for application to the skin of the subject, wherein the device is transformable between an initial state in which the first and second portions are encapsulated within the transcutaneous device unit in an initial sterile state, and a second state in which the second portion is allowed to communicate with the interior of a reservoir through a first portion of the enclosure means and the transcutaneous device portion projects from the mounting surface through a second portion of the enclosure means. For such a device, the two portions and/or the transcutaneous device unit may be moveable as discussed with reference to the above aspect, albeit without the reservoir being part of the device.

By providing a transcutaneous device unit with a mounting surface, the resulting device may advantageously serve as a platform for the mounting of delivery device comprising a drug reservoir and expelling means therefore (e.g. an infusion pump), the platform providing an interface between the reservoir and a subject as well as means for mounting the delivery device on a skin surface of the subject. In this way different delivery devices may be attached to a common platform or a common delivery device may be attached to one of a number of different platforms (e.g. a given platform may interact with the delivery device to select between different infusion properties). Further, the platform may be used as a disposable unit providing a "fresh" transcutaneous device and adhesive surface allowing a given delivery device to be mounted in a convenient way a number of times.

Correspondingly, in a further embodiment the above disclosed platform may be used in combination with a pump unit comprising a reservoir adapted to contain a liquid drug and comprising an outlet means allowing the second portion to be arranged in fluid communication with an interior of the reservoir, and expelling means for, in a situation of use, expelling a drug out of the reservoir and through the skin of the subject via the transcutaneous device. The medical device and the pump unit further comprise mating coupling means allowing the reservoir unit to be secured to the needle unit, the mating coupling means preferably being releasable.

In exemplary embodiments, a fluid communication between the second portion and the reservoir is established when the reservoir unit is attached to the transcutaneous device unit.

In further exemplary embodiments, a fluid communication between the second portion and the reservoir is established and the transcutaneous device portion is moved to a position in which it projects relative to the mounting surface when the reservoir unit is attached to the transcutaneous device unit.

Advantageously, for all of the above discussed embodiments, the mounting surface comprises adhesive means allowing the medical device to be attached to a skin surface of the user.

For all of the above embodiments in which a fluid communication is established between the second portion and a reservoir, this may be provided either via a direct connection between the second portion and the reservoir (e.g. by penetrating a septum of the reservoir) or indirectly (e.g. via connection to a structure in flow communication with the reservoir, e.g. the outlet of a suction pump drawing drug from a reservoir).

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
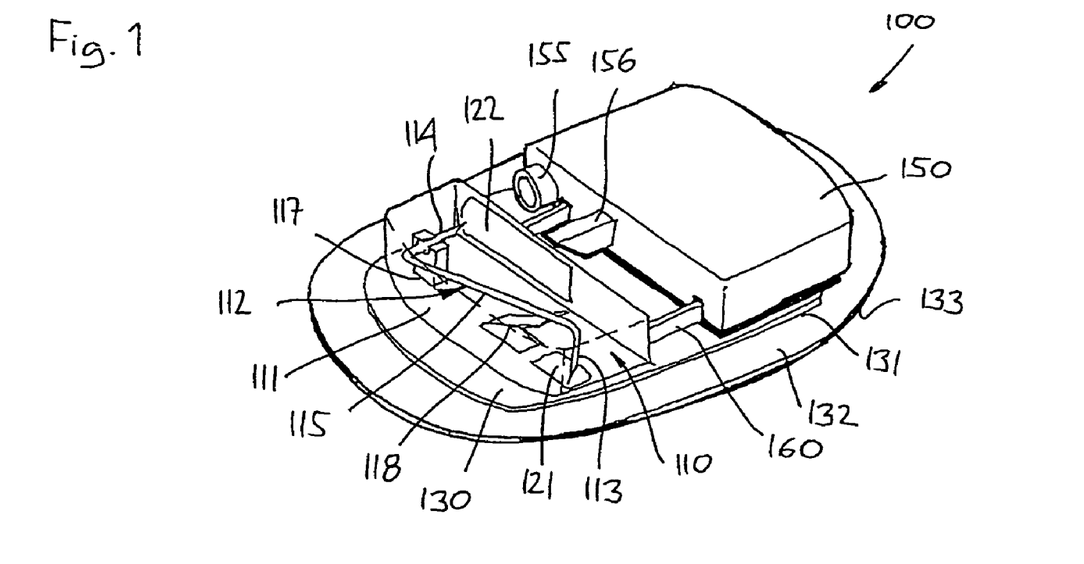
FIG. 1 shows a perspective view of a drug delivery device comprising a first embodiment of a needle unit.

FIG. 1 shows a perspective view of medical device in the form of a drug delivery device in accordance with aspects of the invention. More specifically, FIG. 1 shows a drug delivery device 100 comprising a needle unit 110, a base member 130 with a lower mounting surface 133 adapted for application to the skin of the subject, and a separate pump unit 150. In the shown embodiment the base member comprises a relatively rigid upper portion 131 attached to a more flexible adhesive patch member 132 having a lower adhesive surface providing the mounting surface per se. The needle unit may be formed integrally with the base member or attached thereto as a separate unit, the two elements in combination forming a platform unit. In the shown embodiment the needle unit comprises a housing 111 within which a hollow needle 112 is pivotally arranged. Often, the "downstream" portion of a needle (here: the first portion) is referred to as the distal portion, and the "upstream" portion of a needle (here: the second portion) is referred to as the proximal portion.

The housing comprises first and second openings (or windows) covered by first and second cover means. In the shown embodiment the first cover means is in the form of a needle penetratable rubber membrane 121 and the second cover membrane is in the form of a breakable paper sheet allowing components to be introduced into the interior of the housing. The paper sheet is penetratable to sterilizing gases, the paper sheet, the rubber membrane and the housing in combination providing a sterility barrier for the encapsulated needle portion.

The needle comprises a first needle portion 113 having a first pointed end adapted to penetrate the skin of the subject, the first needle portion extending generally perpendicular to the mounting surface, and a second needle portion 114 in fluid communication with the first needle portion via an intermediate needle portion 115 and having a second pointed end, the second needle portion being arranged substantially in parallel with the mounting surface. The needle is connected to the housing by a mounting member 117 allowing the needle to pivot corresponding to an axis defined by the second needle portion, whereby the needle is moveable between an initial sterile position in which the first needle portion is retracted relative to the mounting surface, and a second position in which the pointed end of the first needle portion projects through the rubber septum and relative to the mounting surface. The housing also comprises a biasing member 118 biasing the needle towards the initial position.

The pump unit 150 comprises a housing in which a reservoir and expelling means are arranged. The reservoir is adapted to contain a liquid drug (e.g. prefilled or adapted to be filled by a user) and comprises an outlet means in the form of a protruding needle penetratable septum 155 adapted to be arranged in fluid communication with the second needle portion. The expelling means (not shown) is adapted for in a situation of use to expel a drug out of the reservoir and through the skin of the subject via the hollow needle. The pump unit further comprises a ramp member 156 arranged next to the reservoir outlet. The reservoir and expelling means may be of any suitable configuration, e.g. as disclosed with reference to FIGS. 7A-7D.

The mounting platform comprises a receiving portion, the receiving portion and the pump unit comprising mating coupling means 160 allowing the pump unit to be secured to the platform unit. The mating coupling means may be releasable allowing a durable or multi-use pump unit to be attached a number of times to a disposable platform unit.

In a situation of use, the platform unit is mounted on the skin of a user (e.g. by adhesive means arranged on the mounting surface) and the pump unit is attached and locked to the platform unit by sliding it into engagement therewith substantially in parallel with the mounting surface. During the latter operation the protruding septum and the ramp member is moved into engagement with the needle, thereby breaking the paper barrier cover 122, during which operation fluid communication is established between the second needle portion and the reservoir, just as the needle is pivoted from its initial to its second position, the first pointed needle end thereby penetrating the rubber membrane and the skin of the user.

After the pump unit has been connected and the needle introduced subcutaneously, the pump can be started. This may happen either automatically as the two units are connected or by separate user-actuatable starting means, e.g. a start button (not shown).

In an alternative embodiment (not shown), the second needle portion may be fixedly (i.e. non-rotationally) attached to the mounting member 117, the intermediate needle portion 115 being elastically bend as it is forced downwardly by the ramp member 156. In such an arrangement the biasing member 118 may be dispensed with.

Figure 2A:
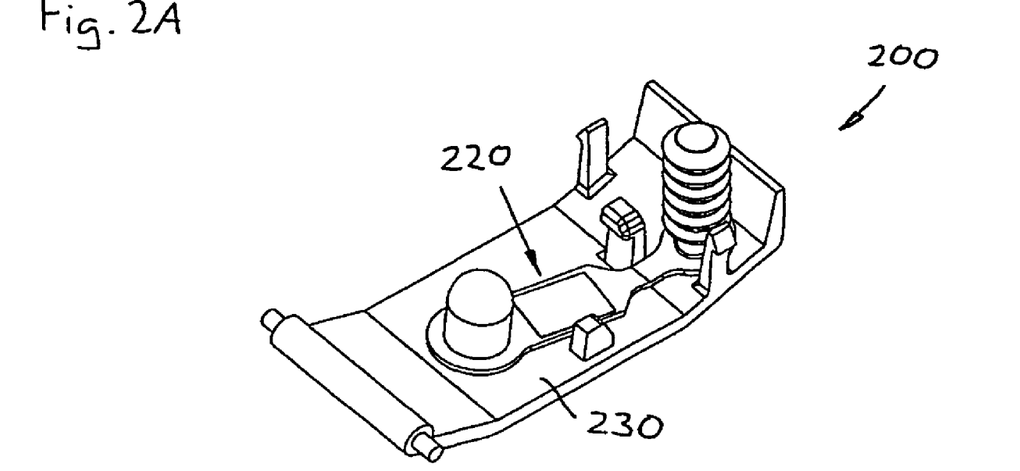
FIG. 2A shows a further embodiment of a needle unit.
Figure 2B:
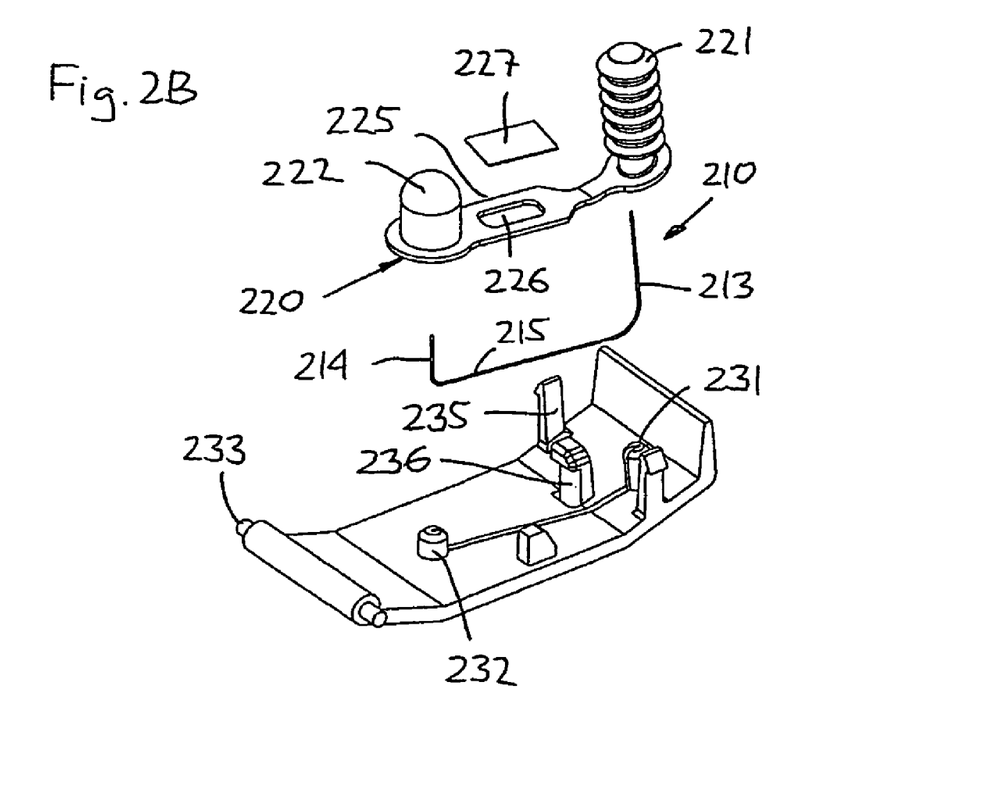
FIG. 2B shows an exploded view of the needle unit of FIG. 2A, FIGS. 3A and 3B show cross-sectionals view of the needle unit FIG. 2A mounted to a drug delivery device.

FIGS. 2A and 2B show a further embodiment of a needle unit. More specifically, FIG. 2A shows a needle unit 200 comprising a needle carrier 230 to which a U-formed needle 210 and a cover member 220 are attached. The needle comprises a first needle portion 213 having a first pointed end adapted to penetrate the skin of a subject, and a second needle portion 214 in fluid communication with the first needle portion via an intermediate needle portion 215 and having a second pointed end, the two needle portion being arranged substantially in parallel with each other corresponding to the legs of the U-formed needle. The carrier comprises gripping means 231, 232 for holding the needle, hinge means 233 allowing the needle unit to be pivotally connected to a delivery device, and a number of hook members 235, 236 intended for engagement with the delivery device (not relevant for the present invention).

The cover member is made from a deformable elastic or non-elastic material and comprises first and second collapsible cover portions 221, 222 encapsulating the first respectively the second needle portions, the cover portions being collapsible from an initial configuration surrounding the needle portions to a collapsed configuration (e.g. in the form of an elastic rubber cover as shown or a telescoping arrangement) wherein the needle portions extend through the cover portions (see below). In the shown embodiment the cover portions are in the form of a bellows and a rounded cylinder, however, they may have any configuration allowing them to collapse. The two cover portions are connected by an intermediate portion 225 which in combination with the carrier forms a conduit providing fluid communication between the first and second enclosures formed by the two cover portions, the intermediate portion comprising a window 226 closed by a paper sheet 227. The paper sheet is penetratable to sterilizing gases (e.g. water vapour or ethylene gas) yet provides a sterility barrier for the encapsulated, this allowing sterilization of the enclosed needle.

Figure 3A:
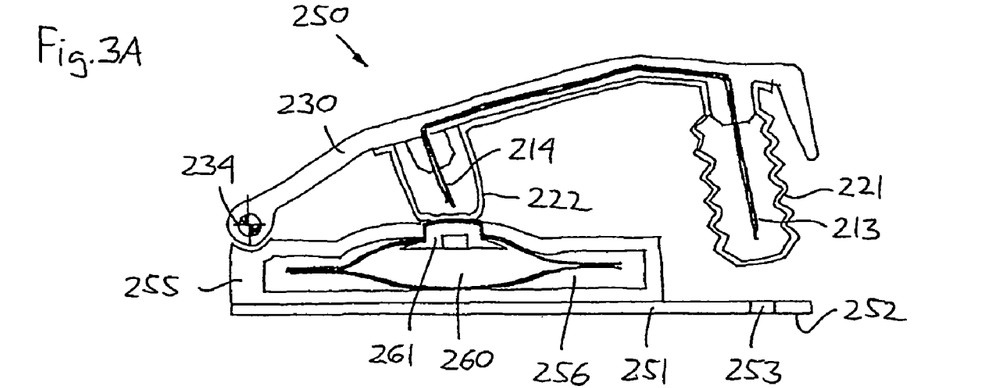
Figure 3B:
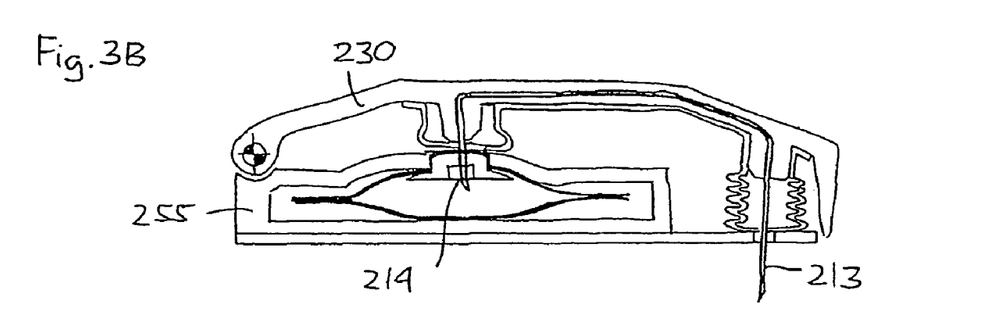

FIGS. 3A and 3B show cross-sectionals view of the needle unit 200 incorporated in a drug delivery device 250. The drug delivery device comprises a base plate 251 with a lower skin mountable surface 252 and an aperture 253, a housing member 255 forming a secondary reservoir 256 containing a drive fluid (see description of the FIG. 7D embodiment below) and in which a flexible, bag-like drug reservoir 260 is arranged, the drug reservoir comprising a needle-penetratable elastomeric septum 261. The needle unit is pivotally connected to the housing member, the carrier 230 thereby forming a lid member. In the shown embodiment the lid member is part of a relatively small needle unit, however, the lid may also be formed integrally with the housing member, the two portions being connected by e.g. a film hinge, in which case the needle unit would incorporate a portion of the drug delivery device.

FIG. 3A shows the delivery device in an initial state in which both of the needle portions 213, 214 are sterily enclosed within the collapsible cover portions 221, 222. FIG. 3B shows the delivery in a state of use in which the lid has been moved into locking engagement with the housing member (by means of the hook members, see FIG. 2A). During this operation the first needle portions is moved through the aperture in the base plate, thereby penetrating the skin of the user when the delivery device has been mounted on a skin surface, and the second needle portion penetrates the reservoir septum to thereby establish fluid communication between the reservoir and the needle. As appears from the figure, during this operation the cover portions 221, 222 collapses as they are moved into engagement with the base plate respectively the septum, the pointed needle portions thereby penetrating the covers. After use the movement of the needle unit may be reversed to thereby withdraw the used needle into the device and de-connect the needle from the reservoir to thereby stop the flow and/or prevent leakage.

Figure 4A:
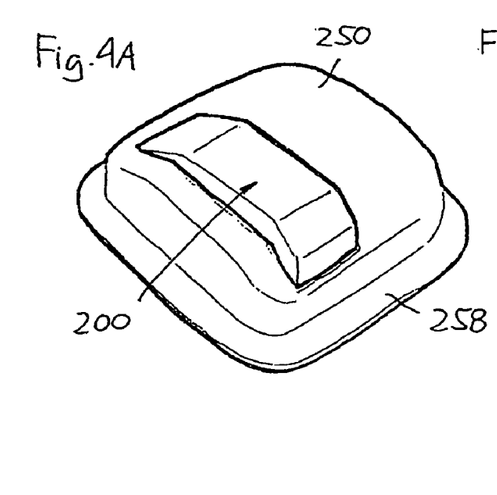
FIGS. 4A and 4B show in perspective views delivery devices corresponding to FIGS. 3A and 3B.
Figure 4B:
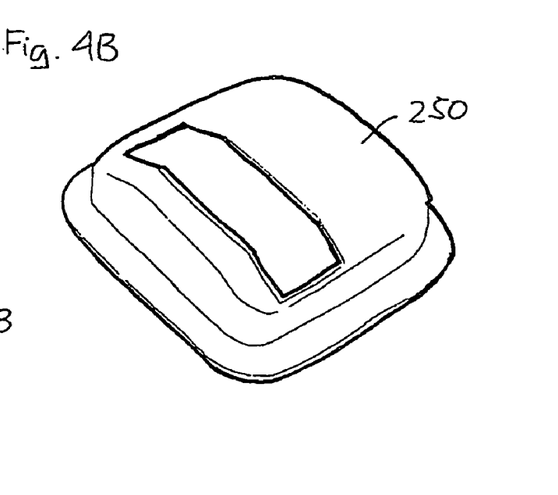

FIGS. 4A and 4B show in a perspective view the same situations as in FIGS. 3A and 3B, with the difference that the base member comprises an adhesive patch portion.

Figure 5:
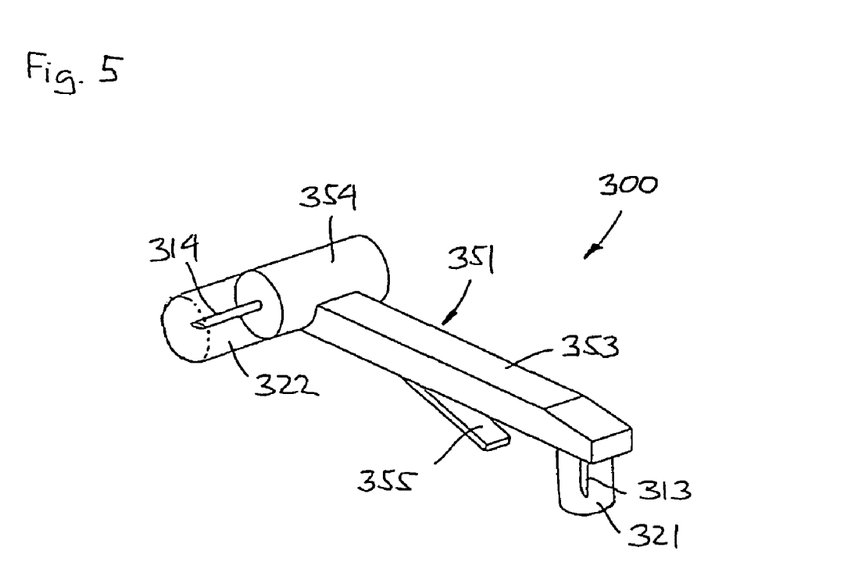
FIG. 5 shows a further embodiment of a needle unit.
Figure 6A:
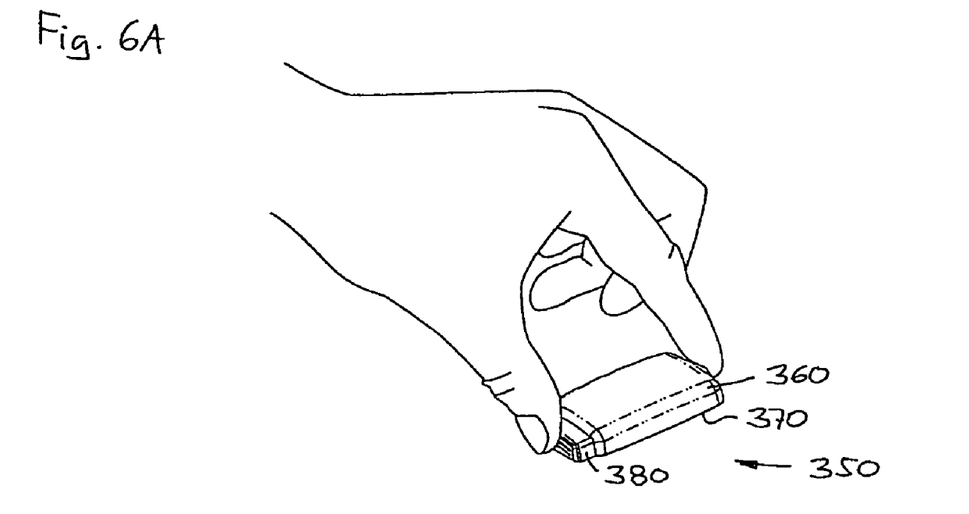
FIG. 6A shows in a perspective view a second embodiment of a medical device gripped by a user corresponding to a first state of use.
Figure 6B:
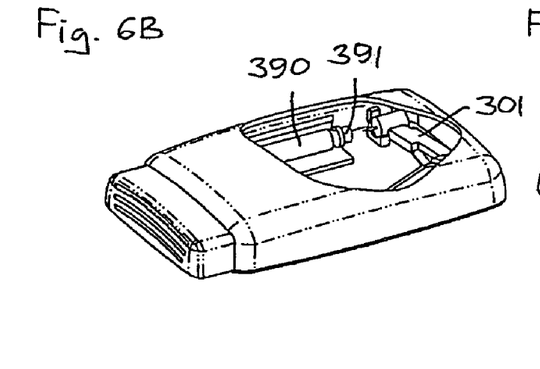
FIG. 6B shows the device of FIG. 4A with a portion of the housing cut off.
Figures 6C, 6E:
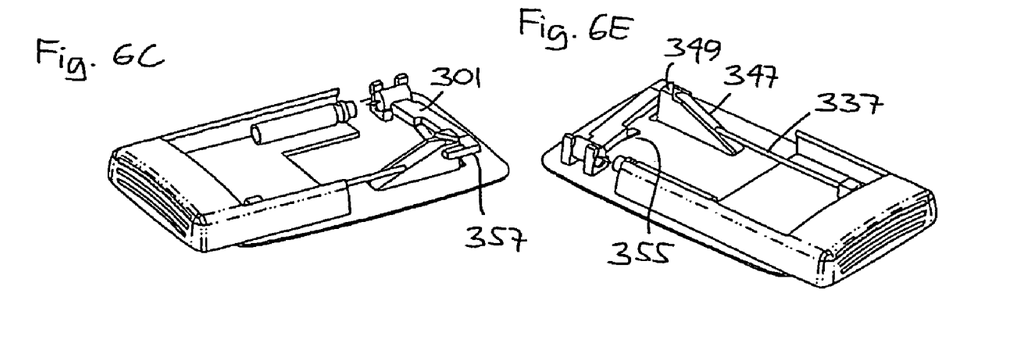
FIG. 6C shows the device of FIG. 4A with a portion of the housing removed.
FIG. 6E shows the device of FIG. 4D with a portion of the housing removed.
Figure 6D:
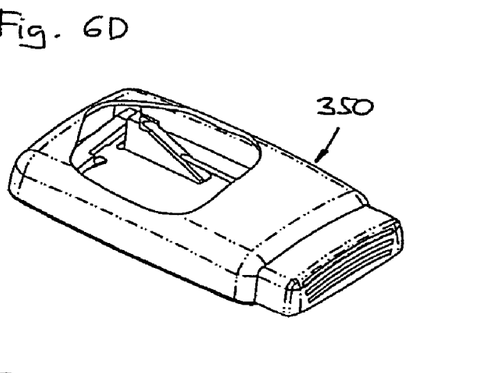
FIG. 6D shows the device of FIG. 4A seen from a different angle with a portion of the housing cut off.

FIG. 5 shows a further embodiment of a needle unit 300 adapted to be connected to a housing member by a hinge allowing the needle unit to pivot corresponding to a pivoting axis defined by the hinge. More specifically, the needle unit comprises a needle carrier 351 having a cylindrical hinge portion 354 defining the pivoting axis, and an arm member 353 extending perpendicularly from the hinge portion in respect of the pivoting axis. On a lower surface of the arm member a biasing means is arranged in the form of a leaf spring member 355 adapted to engage a portion of the housing. The needle carrier carries a needle having first and second pointed portions 313, 314 arranged substantially corresponding to the needle of the needle unit shown in FIG. 1, i.e. with the second needle portion arranged correspondingly to the pivoting axis.

The two needle portions are provided with individual encapsulating cover members 321, 322 maintaining the needle portions in a sterile condition. The cover members may be hollow members being partly or fully made from materials penetratable to sterilizing gases, or they may be in the form of "solid" foam members being either elastic collapsible or non-elastic crushable, such a foam material preferably being penetratable to sterilizing gases yet providing a sterility barrier for the encapsulated needle portions. A similar crushable cover is also discussed in U.S. Pat. No. 6,126, 637, however, for the present invention it is important that such a cover fully meets the relevant requirements as to providing a sterility barrier.

FIGS. 6A-6E show perspective views of the needle unit 301 (substantially corresponding to the needle unit 300 described above) mounted in a drug delivery device 350, however, for illustrative purposes, the needle unit is shown without encapsulating cover members.

More specifically, in FIGS. 6A-6E is shown a second embodiment of a drug delivery device 350, the device comprising an upper housing portion 360 and a lower base plate portion 370 having a mounting surface, the housing providing a cavity in which an actuation member 380 is slidingly received through an opening, the actuation element being moveable corresponding to a longitudinal direction. The device further comprises a reservoir 390 and the needle unit 301. The reservoir is adapted to contain a liquid drug and comprises in a situation of use an outlet in fluid communication with the infusion needle, and cooperate with expelling means (not shown for better illustrating the principles of the needle unit activation) for expelling a drug out of the reservoir and through the skin of the subject via the hollow needle. The reservoir and the expelling means are mounted on the actuation member and thus moveable relative to the housing. The reservoir comprises a needle-penetratable septum 391 adapted to cooperate with the second portion of the needle, the septum being arranged substantially corresponding to the pivoting axis, thereby allowing the needle unit to pivot substantially without non-rotational displacement of the inlet portion of the infusion needle relative to the septum.

The device also comprises an inserter spring 337 and a ramp member 347, the inserter spring being in the form of a thin rod, the ramp member being arranged to deflect the inserter spring upwards as well as sidewards. The ramp surface is somewhat longer and has a concave cross-sectional configuration, this allowing the rod spring to slide thereon without accidental disengagement when the actuation member 380 is pushed into the device. The ramp terminates in an obliquely oriented deflection wall 349 which will force the spring rod outwards when forced there against. The rod may be formed integrally with the actuation member or attached as a separate member, e.g. as a metal string. The needle unit comprises a separately formed engagement portion 357 projecting from the distal end of the carrier arm and arranged on the side of the ramp member just below the deflection wall.

In use, the delivery device is actuated by pushing the actuation member into the device whereby the rod slides up the ramp for subsequently being deflected from the ramp, thereby pivoting the needle unit from its initial position to a position in which the first needle portion extends from the lower surface of the delivery device. At the same time the reservoir is pushed into fluid communication with the second needle portion.

In the above-described embodiments a delivery device has been described comprising a reservoir, however, for better illustrating the principles of the present invention, the means for expelling a drug from the reservoir has been omitted in the figures. Such expelling means, which as the reservoir does not form part of the present invention in its basic form, may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 7A:
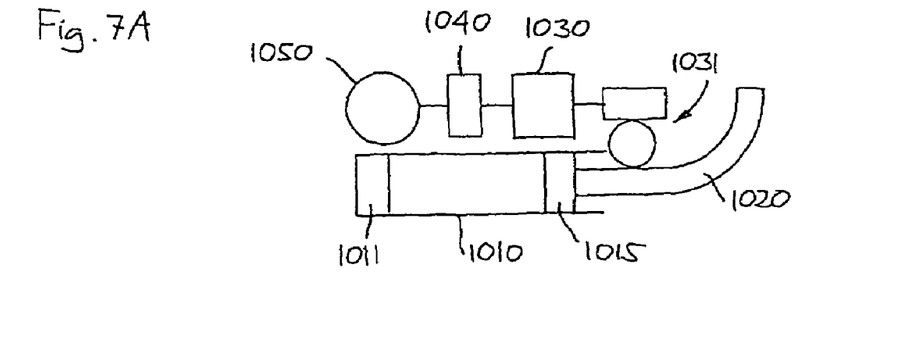
FIGS. 7A-7E shows different expelling means suitable for use with the invention.

In FIGS. 7A-7E examples of expelling means suitable for use with the present invention are shown schematically, however, these are merely examples, just as the shown arrangement of the individual components not necessarily are suitable for direct application in the above shown delivery devices. More specifically, FIG. 7A shows a pump arrangement comprising a drug-containing cartridge 1010 forming a reservoir and having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 7B:
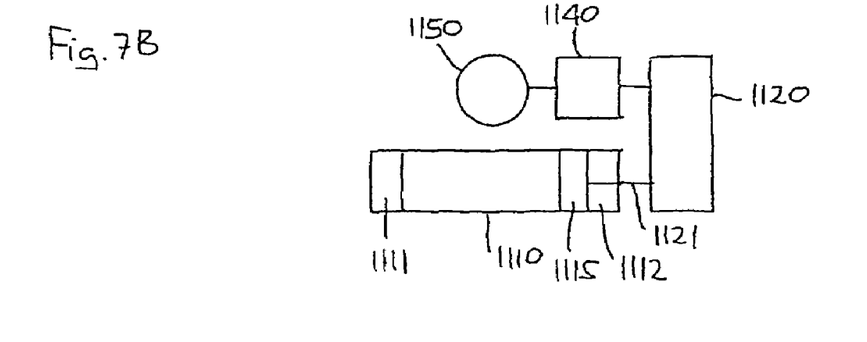

FIG. 7B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 7C:
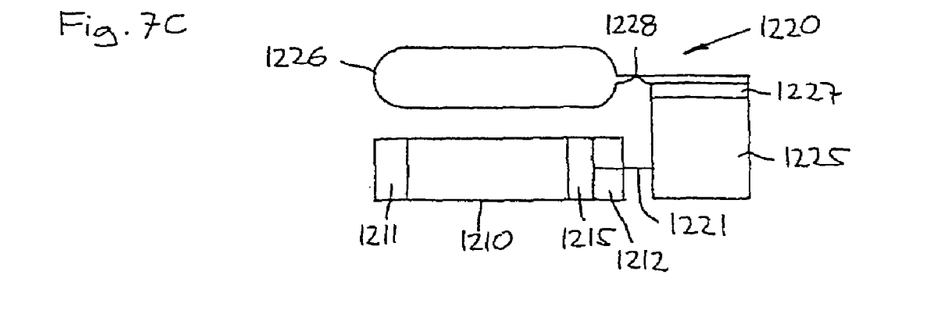

FIG. 7C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semi-permeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 7D:
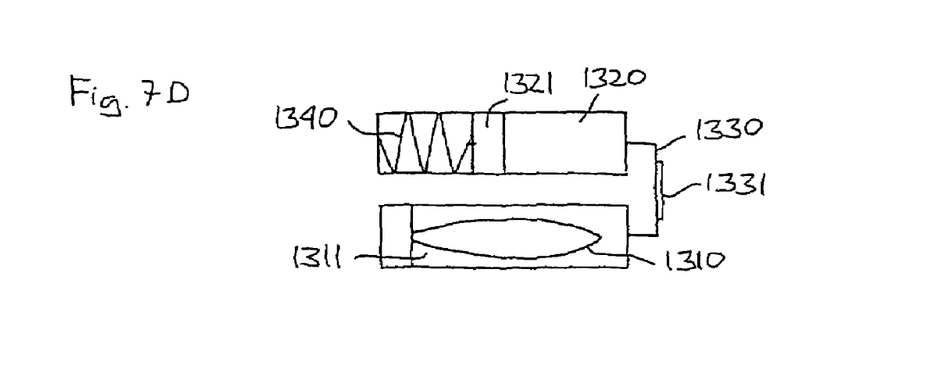

FIG. 7D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring 1340 is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

Figure 7E:
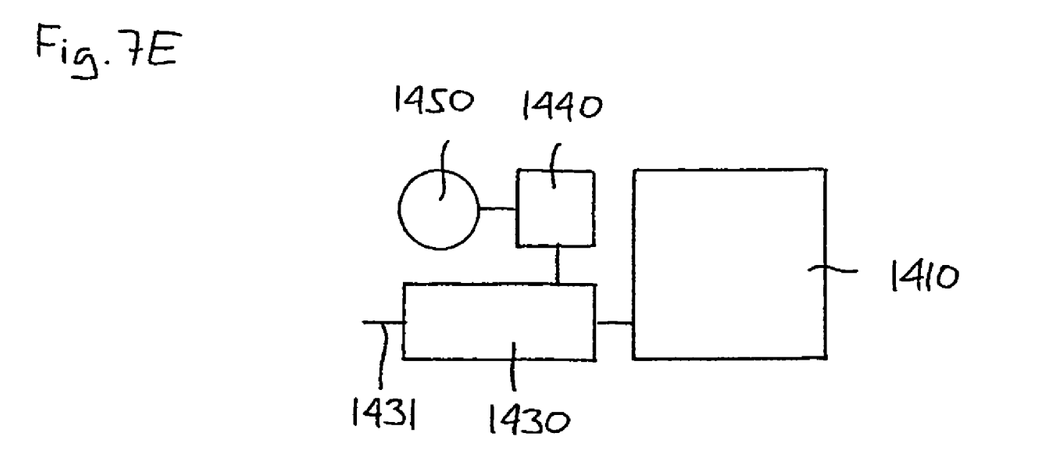

FIG. 7E shows a pump arrangement comprising a membrane pump 1430 having an outlet 1431 and control means 1440 for controlling the pump, the energy for the control means and the pump being provided by a battery 1450. The membrane pump is (in a situation of use) connected to a reservoir 1410 from which drug is sucked through the pump and expelled through the outlet. The reservoir may be provided with venting means or it may be in the form of a flexible, collapsible reservoir whereby venting means can be dispensed with. The pump may be activated when the needle is inserted (by means not shown) or by separate user-actuatable means (not shown) after the inserter has been detached form the delivery device.

In the above described embodiments, the transcutaneous device has been in the form of a unitary needle device (e.g. an infusion needle as shown), however, the transcutaneous device may also be in the form of a cannula in combination with an insertion needle which is withdrawn after insertion thereof. For example, the first needle portion may be in the form of a (relatively soft) infusion cannula (e.g. a Teflon® cannula) and a therethrough arranged removable insertion needle. This type of cannula needle arrangement is well known from so-called infusion sets, such infusion sets typically being used to provide an infusion site in combination with (durable) infusion pumps.

Figure 8A:
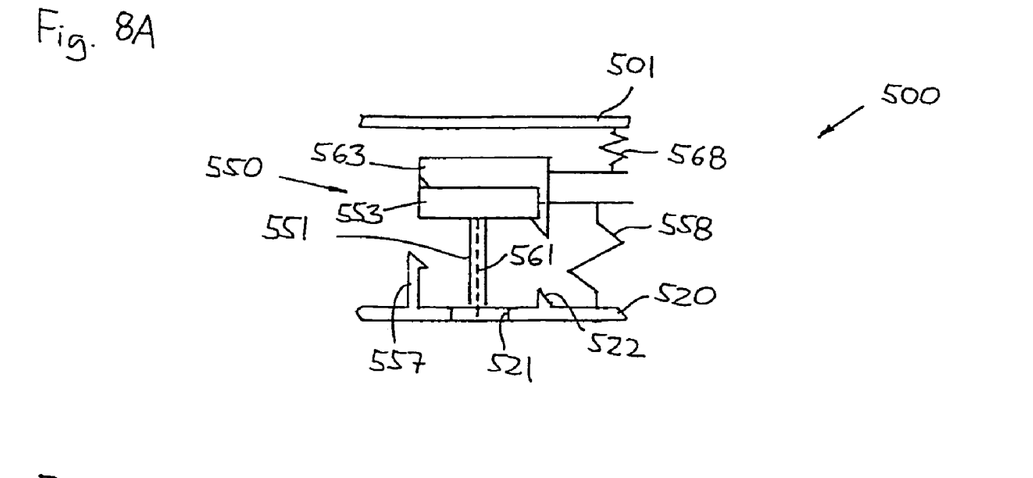
FIGS. 8A and 8B show in a schematic representation a transcutaneous device in the form of a cannula and insertion needle combination.
Figure 8B:
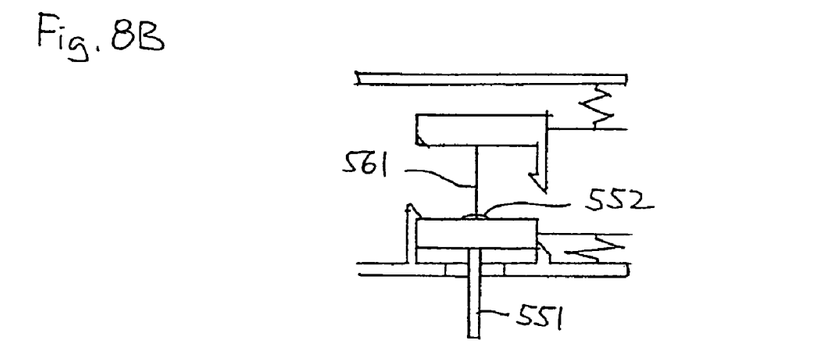

Thus, FIGS. 8A and 8B show in a schematic representation how a cannula and insertion needle combination can be arranged within a housing 501 of a transcutaneous device unit 500, e.g. corresponding to the needle unit 110. More specifically, the medical device comprises a transcutaneous assembly 550 comprising a combination of a relatively soft cannula 551 (which e.g. may be of the soft "Teflon®" type) carried by a lower member 553 and a pointed insertion needle 561 (e.g. made from medical grade stainless steel) slidably arranged within the cannula and carded by an upper member 563, both members being mounted to allow axial displacement of the cannula respectively the insertion needle. The cannula comprises a proximal inlet (not shown) allowing it to be arranged in fluid communication with a fluid source through the enclosure means (not shown). The medical device further comprises a base plate 520 with an initially sealed opening 521 for the cannula as well as a release member 522. The lower member comprises an elastomeric seal 552 through which the insertion needle is arranged. The cannula and the insertion needle may be straight or curved dependent upon how the two members are mounted in the device, e.g. arcuate corresponding to a pivoting axis or straight corresponding to linear movement as illustrated. The upper member comprises a coupling member 567 locking the members together in an initial position with distal end of the insertion needle extending from the distal opening of the cannula as shown in FIG. 8A, and the base plate comprises coupling member 557 for locking the lower member in an extended position with distal end of the cannula extending through the opening in the base plate (see FIG. 8B). Between the housing of the device and the upper member a first spring 568 is arranged biasing the upper member upwards. Correspondingly, the device also comprises a second spring 558 biasing the lower member upwardly.

In a situation of use the assembly is moved downwardly by a suitable actuator (not shown), whereby the cannula with the projecting insertion needle is inserted through the skin of a subject. In this position the lower member engages the coupling member 557 to thereby lock the cannula in its extended position, just as the coupling member 567 is released by the release member 522 thereby allowing the upper member to return to its initial position by means of the first spring.

Figure 9A:
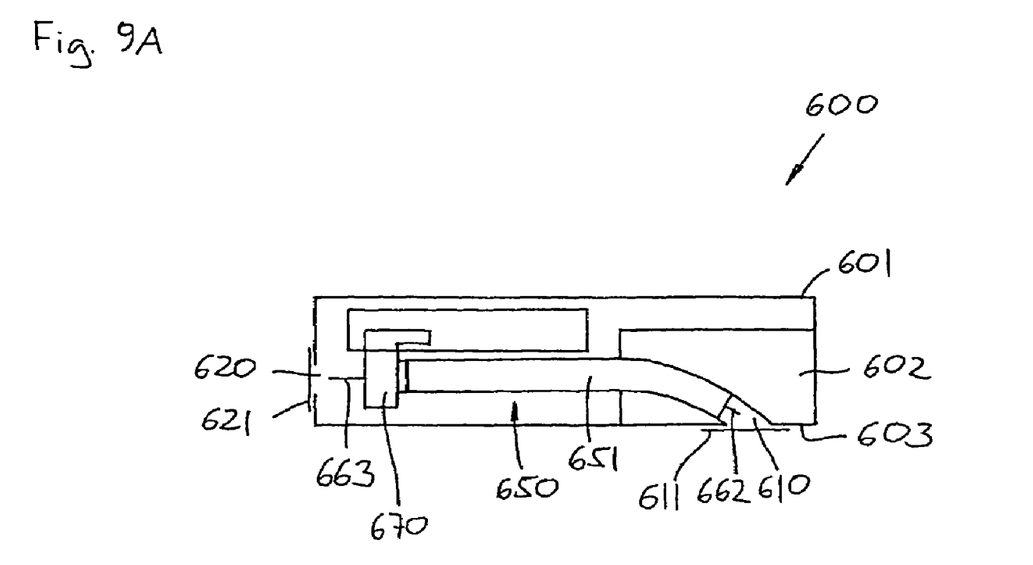
FIGS. 9A and 9B show in a schematic representation a further embodiment of a transcutaneous device in the form of a cannula and insertion needle combination.
Figure 9B:
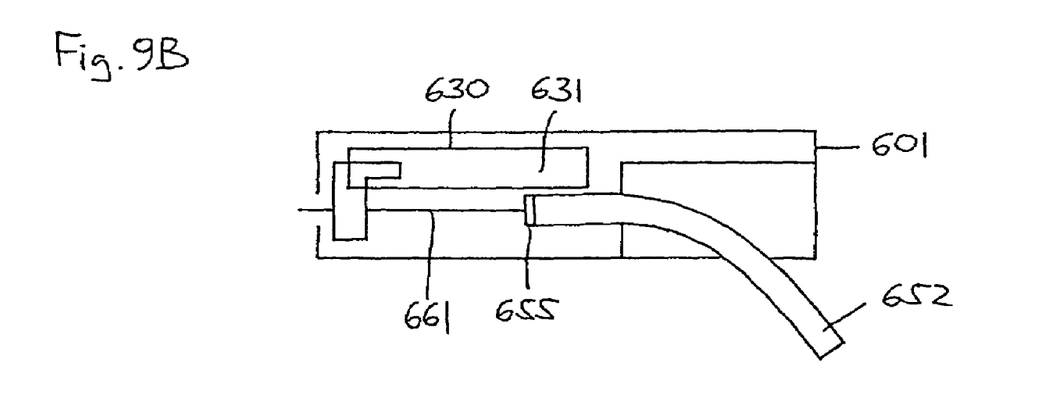

FIGS. 9A and 9B show in a schematic representation a further embodiment of a cannula and insertion needle combination arranged within a housing 601 of a transcutaneous device unit 600, e.g. corresponding to the needle units 110 or 301, the housing having a lower surface 603. More specifically, FIG. 9A shows a medical device unit in an initial state comprising a transcutaneous assembly 650 comprising a combination of a relatively rigid, hollow insertion needle 661 (e.g. made from medical grade stainless steel) and a relatively soft cannula 651 (which e.g. may be of the soft "Teflon®" type) disposed on the insertion cannula. The cannula includes a seal portion 655 which enables the cannula and the needle to move relative to each other while maintaining a seal therebetween. The insertion needle is coupled to an actuation member 670 and has a pointed distal end 662 which in the initial state protrudes from a distal opening in a distal portion 652 of the cannula, and a proximal end 663 adapted to be arranged in fluid communication with a fluid providing structure, e.g. a conduit or directly with a fluid reservoir. The enclosure means ensuring that the transcutaneous assembly can be kept in a sterile state comprises a housing 601 with a guide member 602 for deflecting the transcutaneous assembly during insertion, the housing having three sealed openings (e.g. sealed by breakable paper sheets). A first opening 610 provided with a first seal 611 covers the distal insertable end portion of the transcutaneous assembly, a second opening 620 provided with a second seal 621 covers the proximal end of the insertion needle, and a third side opening 630 provided with a third seal 611 allows an engagement member (not shown and not part of the unit 600) to engage the actuation member and move it corresponding to the longitudinal axis of the non-deflected portion of the insertion needle. In alternative embodiments two or more openings may be combined to a single opening with a single seal member.

The above-described transcutaneous assembly is of the same type as described in WO 03/090509 and WO 02/40083 which are hereby incorporated by reference. This document discloses a number of further transcutaneous assemblies which advantageously may be arranged in a sealed structure corresponding to the present invention.

In a situation of use the transcutaneous device unit (or the device in which it is incorporated) is arranged on a skin surface of a subject and an engagement member is advanced through the third opening 630 thereby engaging the actuation member 670 which can then be moved from an initial (or first) state to an extended state by which both the cannula and the insertion needle is moved to an extended position (the latter being pushed by the actuation member) by which action the combined distal ends of the cannula and the insertion needle penetrate the first seal member and subsequently the skin of the subject. In this position the cannula is locked in place (either reversibly or irreversibly), e.g. by friction or by additional locking means (not shown), where after the insertion needle is withdrawn proximally as shown in FIG. 9B, however, the needle is still in sealed fluid communication with the cannula. In the shown embodiment the insertion needle is withdrawn further proximally compared to its initial position whereby the proximal end of the insertion needle penetrates the second seal member, this allowing connection to a fluid source externally of the unit. The proximal end may be pointed allowing it to penetrate e.g. a self-sealing membrane. In the shown embodiment the transcutaneous assembly is moved by actuation means from the outside, however, energized actuation means (e.g. one or more spring members)

may be included within the housing and adapted to be released by external means, e.g. as shown in WO 03/090509. After use, the actuation means may be adapted to retract the cannula before the device is removed from the skin of the subject.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical device, comprising:
a mounting surface adapted for application to the skin of a subject,
a transcutaneous device portion having a first end adapted to penetrate the skin of the subject, the transcutaneous device portion forming a first portion,
an inlet portion in fluid communication with the first portion and having a second end, the inlet portion forming a second portion, and
enclosure means being transformable from an initial configuration encapsulating the first and second portions in an initial sterile state, to a second configuration in which the first and second ends are allowed to communicate with the exterior through the enclosure means,
wherein the enclosure means does not enclose the mounting surface, wherein the device further comprises:
a generally U-formed hollow needle the legs thereof forming the first and second portions, wherein the U-formed hollow needle is moveable from an initial position, corresponding to the initial state and with the first needle portion retracted relative to the mounting surface, and a second position in which the second needle portion is in fluid communication with the interior of the reservoir and the pointed end of the first needle portion projects relative to the mounting surface, and
wherein the U-formed hollow needle is connected relative to the mounting surface by a hinge allowing the needle unit to pivot from the initial to the second position corresponding to a pivoting axis defined by the hinge, the pivoting axis being arranged substantially in parallel with the mounting surface.

2. A medical device, comprising:
a mounting surface adapted for application to the skin of a subject,
a transcutaneous device portion having a first end adapted to penetrate the skin of the subject, the transcutaneous device portion forming a first portion,
an inlet portion in fluid communication with the first portion and having a second end, the inlet portion forming a second portion, and
enclosure means being transformable from an initial configuration encapsulating the first and second portions in an initial sterile state, to a second configuration in which the first and second ends are allowed to communicate with the exterior through the enclosure means,
wherein the enclosure means does not enclose the mounting surface,
wherein the transcutaneous device portion comprises:
an insertion needle and a cannula disposed on and being axially moveable relative to the insertion needle,
wherein the transcutaneous device portion has a first state in which the first end is in a retracted position within the enclosure means, and a second state in which the first end projects through a portion of the enclosure means, a distal end of the insertion needle projecting from a distal opening in the cannula,
wherein the transcutaneous device portion has a third state in which the distal end of the insertion needle is retracted relative to the distal opening in the cannula.

3. A medical device, comprising:
a mounting surface adapted for application to the skin of a subject,
a transcutaneous device portion having a first end adapted to penetrate the skin of the subject, the transcutaneous device portion forming a first portion,
an inlet portion in fluid communication with the first portion and having a second end, the inlet portion forming a second portion, and
enclosure means being transformable from an initial configuration encapsulating the first and second portions in an initial sterile state, to a second configuration in which the first and second ends are allowed to communicate with the exterior through the enclosure means,
wherein the enclosure means does not enclose the mounting surface,
wherein the transcutaneous device portion comprises:
an insertion needle and a cannula disposed on and being axially moveable relative to the insertion needle wherein the insertion needle comprises a proximal end forming the inlet portion, a seal being formed between the insertion needle and the cannula providing a fluid communication between the proximal end of the insertion needle and the distal opening in the cannula.

4. A transcutaneous device unit, comprising:
a transcutaneous device portion having a first end adapted to penetrate the skin of a subject, the transcutaneous device portion forming a first portion,
an inlet portion in fluid communication with the first portion and having a second end, the inlet portion forming a second portion, and
enclosure means being transformable from an initial configuration encapsulating the first and second portions in an initial sterile state, to a second configuration in which the first and second ends are allowed to communicate with the exterior through the enclosure means,
wherein the transcutaneous device portion comprises an insertion needle and a cannula disposed on and being axially moveable relative to the insertion needle, wherein the transcutaneous device portion has a first state in which the first end is in a retracted position within the enclosure means, and a second state in which the first end projects through a portion of the enclosure means, a distal end of the insertion needle projecting from a distal opening in the cannula,
wherein the transcutaneous device portion has a third state in which the distal end of the insertion needle is retracted relative to the distal opening in the cannula, and
wherein the insertion needle is hollow and comprises a proximal end forming the inlet portion, a seal being formed between the insertion needle and the cannula providing a fluid communication between the proximal end of the insertion needle and the distal opening in the cannula.

5. A transcutaneous device unit, comprising:
a transcutaneous device portion having a first end adapted to penetrate the skin of a subject, the transcutaneous device portion forming a first portion,
an inlet portion in fluid communication with the first portion and having a second end, the inlet portion forming a second portion, and enclosure means being transformable from an initial configuration encapsulating the first and second portions in an initial sterile state, to a second configuration in which the first and second ends are allowed to communicate with the exterior through the enclosure means, wherein the transcutaneous device portion comprises an insertion needle and a cannula disposed on and being axially moveable relative to the insertion needle, wherein the transcutaneous device portion has a first state in which the first end is in a retracted position within the enclosure means, and a second state in which the first end projects through a portion of the enclosure means, a distal end of the insertion needle projecting from a distal opening in the cannula, and wherein the transcutaneous device portion has a third state in which the distal end of the insertion needle is retracted relative to the distal opening in the cannula, and wherein the unit further comprising a deflecting structure, whereby a distal portion of the cannula is deflected relative to a proximal portion of the cannula as the cannula is moved from the retracted to the projecting position.

* * * * *